United States Patent [19]

Chimowitz et al.

[11] Patent Number: 5,305,232
[45] Date of Patent: Apr. 19, 1994

[54] CHROMATOGRAPHY SYSTEM

[75] Inventors: Eldred H. Chimowitz, Brighton, N.Y.; Frank VanPuyvelde, Tielt, Belgium

[73] Assignee: The University of Rochester, Rochester, N.Y.

[21] Appl. No.: 882,321

[22] Filed: May 13, 1992

[51] Int. Cl.$^5$ ............................................. B01D 15/08
[52] U.S. Cl. ................................... 364/498; 364/500; 210/386; 96/102; 95/82; 95/26
[58] Field of Search ....................... 364/498, 499, 500; 55/67; 210/198.2, 386

[56] References Cited

U.S. PATENT DOCUMENTS

| | | | |
|---|---|---|---|
| 4,714,526 | 12/1987 | Pennisi et al. | 203/49 |
| 5,108,597 | 4/1992 | Funkenbusch et al. | 210/198.2 |
| 5,132,938 | 7/1992 | Walters | 367/94 |
| 5,135,549 | 8/1992 | Phillips et al. | 55/67 |
| 5,180,487 | 1/1993 | Saito et al. | 210/198.2 |
| 5,195,026 | 3/1993 | Nonaka et al. | 364/148 |
| 5,196,039 | 3/1993 | Phillips et al. | 55/67 |

OTHER PUBLICATIONS (Thesis) "Separation in Packed Beds Using Supercritical Fluids", Catholic University Leuven, Van Puyvelde, Jan. 1992.

"Retention and Resolution in Density-Programmed Supercritical Fluid Chromatography", Wilsch and Schneider (1986), J. Chromatography, pp. 239-252.

"Near-Critical Phenomenon and Resolution in Supercritical Fluid Chromatography", Kelley and Chimowitz, AIChE Journal, vol. 36, No. 8, Aug. 1990, pp. 1163-1175.

"A New Representation for Retention Time in Supercritical Fluid Chromatography", Chimowitz and Kelley, J. Supercritical Fluids, 1989, 2, pp. 106-110.

"Advanced Process Control", W. H. Ray, McGraw-Hill Books, p. 88 et seq. (1981).

"Introduction to Linear and Non-Linear Programming", Luenberger, Addison-Wesley Publishing, pp. 33 et seq., (1973).

"An Algorithm for the Simulation of Density-Programmed Supercritical Fluid Chromatography", VanPuyveld and Chimowitz, J. Supercritical Fluids, 1990, 3, pp. 127-135.

"A Variational Solution of the Optimal Resolution Problem in SFC", Groves, VanPuyvelde and Chimowitz, May 22, 1991.

*Primary Examiner*—Thomas G. Black
*Assistant Examiner*—Tan Q. Nguyen
*Attorney, Agent, or Firm*—M. Lukacher

[57] ABSTRACT

A system (method and apparatus) for optimizing the relationship between resolution and time in chromatograms, especially chromatograms obtained by supercritical fluids (CSF) chromatography. The pressure or temperature or fluid density of the solution caring the material under analysis is varied dynamically under computer control to provide an optimum capacity factor for a particular transporting fluid in a particular chromatographic system to obtain the resolution of interest in the shortest period of time.

21 Claims, 7 Drawing Sheets

```
┌─────────────────────────────────────────────────┐
│ GUESS INITIAL TEMPERATURE PROFILE T(t) OVER TIME│
│ INTERVAL [t₀,t_f] WHERE t_f IS TOTAL TIME OF ANALYSIS│
└─────────────────────────────────────────────────┘
                      │
      ┌───────────────▼───────────────────────────┐
      │ USING TEMPERATURE PROFILE T(t) INTEGRATE  │
      │ MODELING EQUATION FOR EACH COMPONENT j    │
      │                                           │
      │   $\dfrac{dx_j}{dt} = \dfrac{1}{1+K_j}\left(\dfrac{m_0}{A\rho}\right)$ │
      └───────────────┬───────────────────────────┘
                      │
      ┌───────────────▼───────────────────────────────────┐
      │ USING TEMPERATURE PROFILE T(t) AND EVOLUTION OF   │
      │ PEAKS $x_j(t)$, CALCULATE LANGRANGEAN MULTIPLIERS │
      │ BACKWARD IN TIME OVER $[t_0, t_f]$                │
      │                                                   │
      │  $\dfrac{d\lambda_1}{dt} = -(2(x_1 - x_2 - \Delta_1))$ │
      │  $\dfrac{d\lambda_j}{dt} = -2(x_j - x_{j+1} - \Delta_j) + 2(x_{j-1} - x_j - \Delta_{j-1})$ │
      │                              $(1 \ne j \ne N)$    │
      │  $\dfrac{d\lambda_N}{dt} = -(-2(x_{N-1} - x_N - \Delta_{N-1}))$ │
      └───────────────┬───────────────────────────────────┘
                      │
      ┌───────────────▼───────────────────────────────────┐
      │ CALCULATE CORRECTION IN TEMPERATURE PROFILE       │
      │  $\dfrac{\delta H}{\delta T} = \sum\limits_{j=1}^{N} \lambda_j(t)\dfrac{d\phi_j}{dT}$ WHERE $\dfrac{d\phi_j}{dT} = \dfrac{\delta}{\delta T}\left(\dfrac{1}{1+K_j}\dfrac{m_0}{A\rho}\right)$ │
      └───────────────┬───────────────────────────────────┘
                      │
      ┌───────────────▼───────────────────────────┐
      │ USE 1-DIMENSIONAL SEARCH TECHNIQUE TO DETERMINE │
      │ OPTIMAL SCALING FACTOR $\varepsilon_{OPT}$│
      └───────────────┬───────────────────────────┘
                      │
      ┌───────────────▼───────────────────────────┐
      │ ADJUST TEMPERATURE PROFILE                │
      │  $T(t)^{NEW} = T(t)^{OLD} - \varepsilon_{OPT}\dfrac{\delta H}{\delta T}$ │
      └───────────────┬───────────────────────────┘
                      │
      ┌───────────────▼───────────────────────────┐
      │ IS DIFFERENCE BETWEEN $T(t)^{NEW}$ AND $T(t)^{OLD}$ SMALL? │
      └───────┬───────────────────────────┬───────┘
         NO   │                           │ YES
              │                           ▼
              │        ┌──────────────────────────────┐
              │        │ CONVERGED: $T(t)^{OPTIMAL}$  │
              │        └──────────────────────────────┘
              └─(loop back up)
```

FIG. 7

CHROMATOGRAPHY SYSTEM

FIELD OF THE INVENTION

The present invention relates to a system (apparatus and method) for chromatography, and more particularly to a chromatographic system for automatically and objectively optimizing the relationship between resolution and analysis time in chromatographic analyses (i.e., in the chromatogram produced by the system).

The invention is especially useful in supercritical fluid chromatography (SCF).

BACKGROUND

Chromatography is an instrumental procedure, used for separating and analyzing the chemical composition of chemical mixtures based upon physical adsorption principles, which is used widely for organic, chemical, biological and medical studies. Chromatography depends upon the selective retardation and separation of substances by a stationary bed of porous sorptive media (the substrate) as they are transported through a column containing the substrate by a moving transport fluid (which may be, for example, gas, liquid or supercritical fluid). The rate of migration of each substance being tested is determined by its relative partitioning affinity between the substrate and the particular transport medium at the particular flow rate of transport medium being used. A detector positioned at the end of the column generates an analog signal from which quantitative and qualitative information can be derived. A time record (or spectrum) of the detector signal is called a chromatogram, and is a signature of the composition being analyzed. This record contains lines, usually in the form of Gaussian peaks. The amplitudes and time spacing (distance) between peaks are characteristic of the substances being analyzed. The resolution of a chromatogram is determined by the distance separating the means of these peaks on the chromatogram as well as the spread of the peak about the peak mean. Since the chromatogram is a function of time, resolution, which is basically based upon the distance between peaks on the chromatogram, increases as the time needed to transport the sample through the column is increased. Consequently, there is a trade off between resolution and time. To obtain ultra high resolution, the chromatographic analyses must be slowed to a relatively slow speed. Conversely, when relatively lower resolution are sufficient, relatively faster analysis times may be employed. However, in many instances, ultra high resolution is not needed, in which case it is desirable to speed up the transport process, so that the analyte solute species will emerge from the column more quickly. This may be done by changing or altering certain properties of the transport fluid, such as, for example, density, in the case of supercritical fluid chromatography.

In the past, to obtain a certain resolution in the fastest time for a given combination of sample substrate and transporting fluid, etc., the alteration needed to be applied to the particular transport fluid could only be arrived at by trial and error methods. Supercritical fluids have the ability to change density markedly when the temperature or pressure is changed. Consequently, by manipulating the temperature and/or pressure in a supercritical fluid chromatography system, the relative affinity for the solutes partitioning between the solid phase and a supercritical fluid can be controlled. This inherently affects the resolution obtained and the transport time of analytes through the column. However, to arrive at the optimum pressure, temperature and density combination needed for a given supercritical fluid and material under analysis, a great deal of trial and error experimentation was still necessary, even for supercritical fluid chromatography. For example, see Retention and Resolution in Density-Programmed Supercritical Fluid Chromatography, by Wilsch and Schneider, J. Chromatography, Vol. 357, pp. 239-252 (1986).

BRIEF DESCRIPTION OF THE DRAWINGS

The objects, features and advantages of the invention, as well as the best known mode for practice thereof, will become more apparent from a reading of the following detailed description which makes reference to the following drawings:

FIGS. 6, 7 and 8 are flow charts illustrating the programming of the computer in the system shown in FIG. 1 for different causes where the transport fluid is a SCF, a gas and a liquid, respectively.

SUMMARY OF THE INVENTION

In accordance with the present invention, a system (method and apparatus) is provided for use in chromatography, in which the relationship between the resolution of the chromatograph and the time necessary to achieve suitable resolution is optimized dynamically under computer control in advance of the chromatographic analysis. The apparatus includes a column, having a stationary phase, or substrate, and a mobile phase, or transporting fluid. The mobile phase or transporting fluid has a capacity factor k which represents the ability of the mobile phase to transport a species (the material under test) through the column. A detector measures the eventual appearance of the species from the column and provides outputs corresponding to passage of a species in an output signal level. This output is processed to provide data representing the temporal relation among the peaks. During this period a computer may be utilized to dictate how to control the process operating variables so that they conform to the optimized relationships mentioned above. The method of the present invention may be utilized with any form of chromatography, although it is particularly suitable for supercritical fluid chromatography using a SCF as the transport fluid.

DETAILED DESCRIPTION OF THE INVENTION

In accordance with the present invention, a system (method and apparatus) is provided for use in chromatographic analyses in which the relationship between the resolution of the resultant chromatograph and the time needed to achieve that resolution is adjusted sufficiently to meet analytical requirements of the user. Thus, the adjusted resolution vs. time relationship is referred to as being optimized herein. In all chromatographic operations, the resolution of the resultant chromatograph is a function of the time period spent by the particular analyte in the column. Thus, for particularly high resolution chromatographs, the analytes must stay in the column for a relatively long period of time, and consequently, the chromatographic analysis itself is relatively slow. Ultra high resolution may not be needed in many instances, however, and in any event, it is usually desirable to obtain the desired resolution (whether high or low) in the least amount of time. For this reason, the properties of the transporting fluids are commonly manipulated to decrease the time spent by the analyte in the column so that ideally the desired amount of resolution can be achieved in a minimum amount of time.

Supercritical fluid chromatography is a particularly suitable process for use in accordance with the present invention, because the density of the supercritical transport fluid is easily manipulated by adjusting either the temperature or the pressure or both. A particularly preferred supercritical fluid is $CO_2$, because it is non-toxic, non-flammable, and its critical temperature is in the range of about 31° C. (and therefore wont's damage heat degradable compounds).

Figure 1:
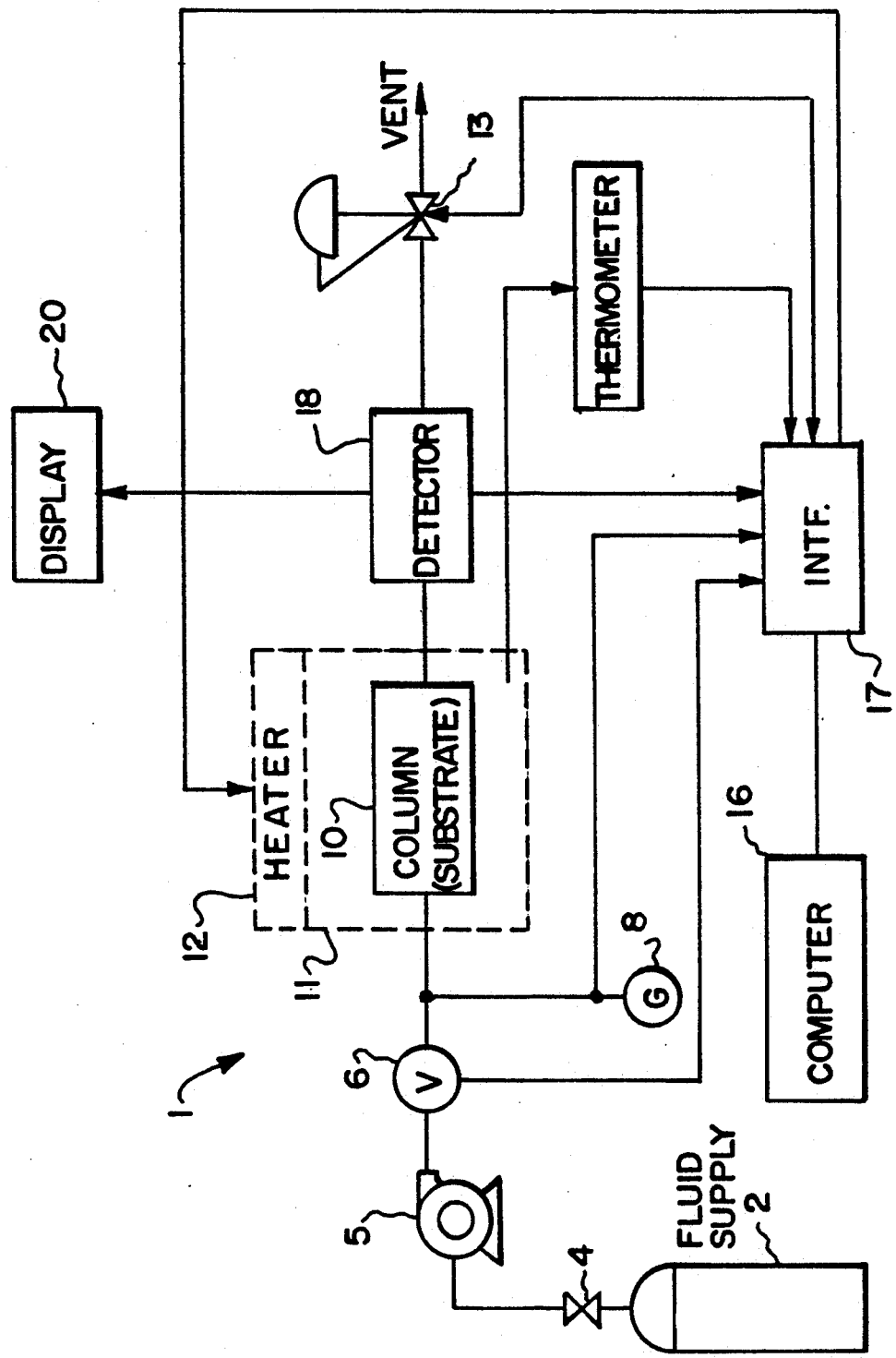
FIG. 1 is a schematic diagram of a typical supercritical fluid chromatographic apparatus embodying the present invention.

A typical apparatus 1 for supercritical chromatography, in accordance with the present invention is illustrated in FIG. 1 and includes a supply 2 of pressurized transporting fluid (a pressure vessel or tank). The discharge of transport fluid from supply 2 is controlled by valve 4. A pump 5 drives the fluid for pressure control as explained below. An injector valve 6 is provided to inject analyte samples into the transporting fluid stream. A pressure gauge 8 is provided for monitoring the pressure of the system. The transport fluid stream is directed through a column 10, which contains the substrate or stationary stage, upon which the sample being analyzed will adsorb. The column is in an enclosure 11 which may be maintained at a desired temperature by a heater 12. A back pressure regulator 13 is provided for adjusting the pressure in the column 10. Thus, the pressure in the column (and therefore the density of the SFC transport fluid) may be altered by manipulating, for example either the back pressure regulator 13 or the pump 5.

The pump 5 and/or the back pressure regulator may be manually adjustable, or preferably, are electrically controllable. Control is provided by the computer or data processor controller 16 via an interface 17 containing digital to analog converters capable of translating the computer digital output to an analog control signals. This interface also digitizes analog signal inputs for processing in the controller 16. As mentioned above, the sample to be analyzed is injected into the stream of transporting fluid via the injector valve 6. The transporting fluid carries the sample to be analyzed into the column 10 where the sample then adsorbs onto the substrate inside column 10. For a given substrate under given conditions, each material (also called the analyte or compound or sample) under analysis has a characteristic retention time within the column which can be used for identification of the compound. Extensive compilations of individual compound-retention times on different substrates for different transport fluids are available in the literature for reference.

Figure 2:
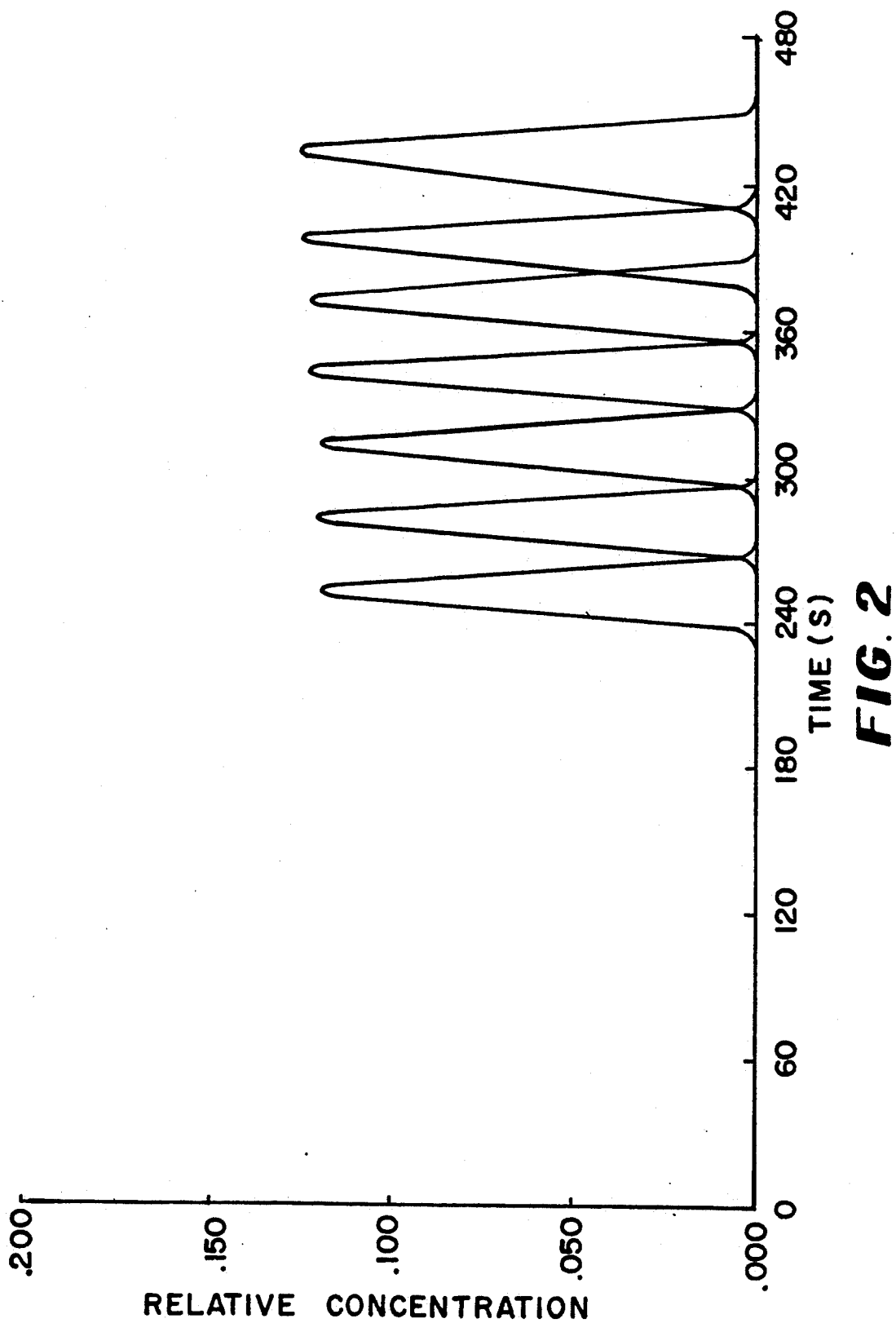
FIG. 2 is an illustration of a typical chromatogram arrived at by using trial and error gradient methods.

A detector 18 is provided at the end of the column. The detector 18 is capable of generating an analog signal based on the retention time in the column, that is proportional to the concentration of the sample component in the moving (mobile) phase. This time record (or chromatogram) may be provided in response to the detection signal or it may be generated by the computer 16 and displayed on a (display 20 which may be a) terminal or recorder (recording means) operated by the computer. Since the retention time represents the capacity of k factor, the detector provides from the chromatogram the k factor for each analyte species. See equations (1) to (3) below. Time records of the detector signal are called chromatograms. A typical chromatogram is illustrated in FIG. 2. A valve (not shown) is provided to allow the transport fluid an sample to be discharged or vented from the system 1. The program stored in the computer 16 is used to dynamically determine the shortest analysis time that may be used to obtain a given degree of resolution, for a given combination of analyte, transport fluid, and substrate in a chromatographic system. Consequently, the relationship between resolution and time can be effectively manipulated to optimize the relationship. The computer may be configured to receive information directly from the chromatographic system (the chromatogram) as shown or, alternatively, may not by physically connected to the system, in which case inputs would be received from the user operating the system.

The ability of a particular substrate to adsorb a particular analyte in the presence of a particular transport fluid is represented by the adsorption or capacity value factor k, which represents the strength with which an analyte adsorbs on the surface of a substrate. Depending on which type of chromatography is being used (gas, liquid, SFC, etc.), the capacity factor K can be altered by changing the density, composition, temperature, and/or pressure of the transport fluid. This alteration affects the resolution and time of analysis for the process.

Figure 6:
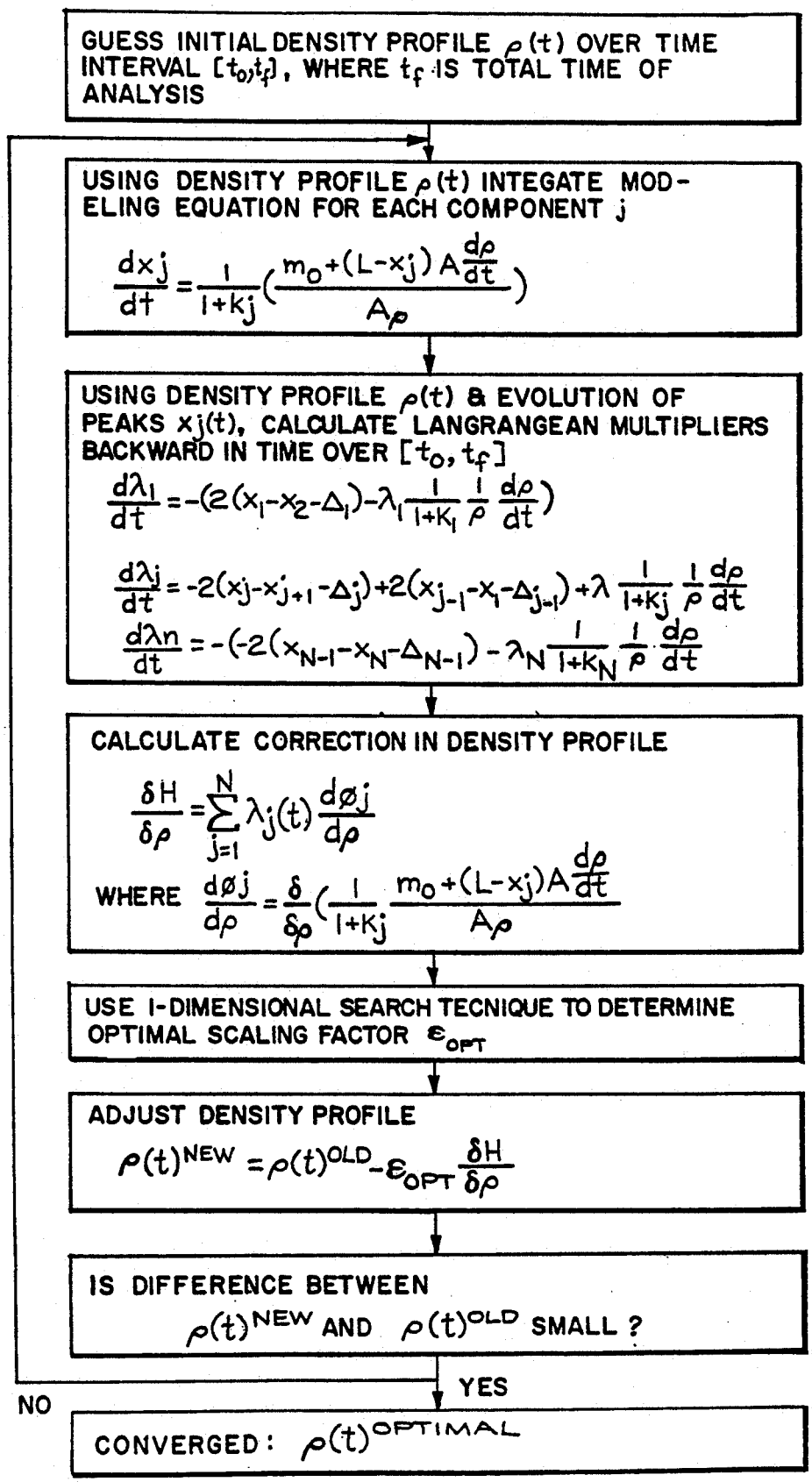
Figure 8:
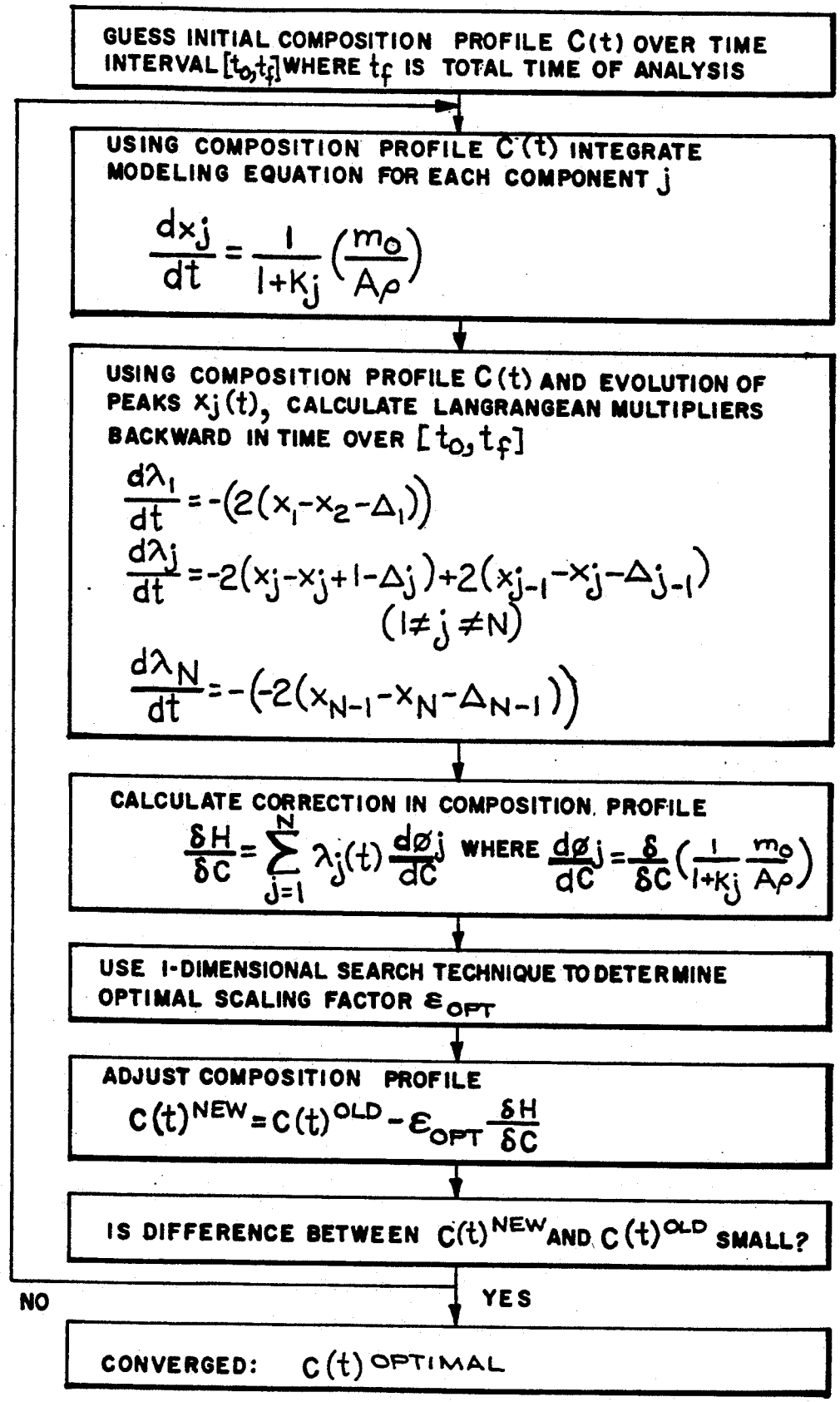

In supercritical fluid chromatography (SFC) a distinct advantage is the ability to control the transport fluid density (and consequently the ability to transport an analyte through a column) with small changes in temperature and/or pressure. This phenomenon only occurs when the transport fluid is near its critical point and does not occur when the fluid material is in either the gas or liquid state; hence this feature makes SFC a potentially more powerful analytical/separations technology than gas chromatography (GC), liquid chromatography, high performance liquid chromatography (HPLC) or any other chromatography technique. SFC is a relatively new technology that has a number of advantages over GC and HPLC. The invention is applicable to SFC, GC, LC and HPLC by utilizing programs adapted specifically thereto as shown in FIGS. 6, 7 and 8, respectively.

Figure 3:
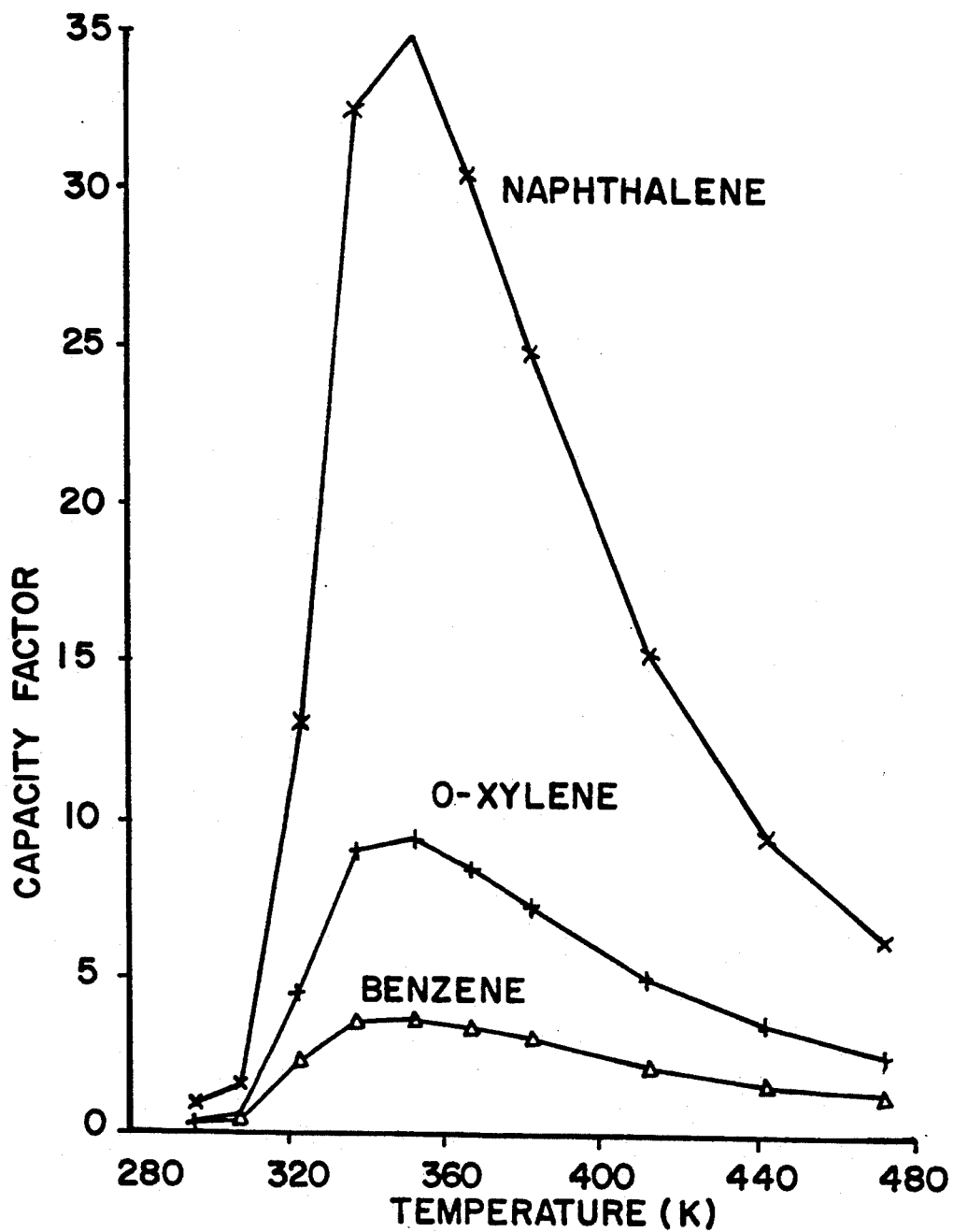
FIG. 3 are curves which illustrate the capacity factor vs. temperature for an analyte species in $CO_2$ supercritical fluid.

FIG. 3 illustrates thermodynamic adsorption coefficient or capacity factor (k-value) data vs. temperature for some polycyclic aromatic analyte species dissolved in a supercritical fluid at a given pressure. The supercritical fluid in this case is carbon dioxide. Similar curves would result for different pressure (and temperature ranges) within the supercritical range of the transport fluid. FIG. 3 thus illustrates the ability of a particular species to adsorb onto the substrate in the column, in the presence of a particular supercritical fluid (in this case $CO_2$) at different temperatures. It is evident from FIG. 3 that the maximum divergence between these coefficients occurs as the critical point of carbon dioxide is approached and traversed. Importantly from a chromatographic standpoint, this region where the differences between component K-values are largest also corresponds to the region of maximal intrinsic resolution of species, which is one of the central purposes of chromatographic analysis of the present invention. This general region is called the $T_{max}$ region (approximately 340°–350° K. for all the species in FIG. 3). This region has been recognized as a property of SFC. See Near-Critical Phenomena and Resolution in Supercritical Fluid Chromatography, Alche J., Vol. 36, No. 8, 1163 (Kelley and Chimowitz, 1990). However, a significant drawback to operating near the $T_{max}$ region is that it is also the regime at which all the species migrate at the slowest rate through the system. From a chromatographic viewpoint this can amount to a severe disadvantage since time of the analysis is an important consideration; in general the shorter the time of analysis, the better, as long as satisfactory resolution is achieved.

Consequently, operating the chromatographic column at the temperature corresponding to $T_{max}$ at a constant pressure is in some respects undesirable because of the slow analysis time. This has led to the development of what are generally referred to in the art as gradient methods. Gradient methods refer to a class of trial and error techniques whereby certain variables (not including time of analysis) of the chromatographic operation are first guessed. The guessed parameters such as, for example, pressure and temperature (and thus, inherently, density) of the mobile phase in a SFC system are then used in a chromatographic system, after which the resultant chromatogram is studied to determine if more or less resolution is needed. A second guess for variable parameters is then made, after which the resultant chromatogram is again studied, and so on until finally the variables are guessed which result in adequate resolution within an adequate analysis time. At this point, the system performance is said to be optimized. Optimization is thus where the resolution of interest is obtained in a satisfactory time. Obviously, gradient methods can be very time consuming.

For simplicity of explanation, much of the discussion herein is directed specifically to SFC. However, it should be understood that the invention is in no way limited to SFC, and thus may be easily tailored, by those skilled in the art, to be operable for any form of chromatography. Further, even as explained herein for SFC application, the invention could be tailored to work differently without departing from the spirit and scope of the invention. For example, more than one supercritical fluid (such as, for example, a mixture of $CO_2$ and ethane) could be utilized as the SFC transport fluid.

In accordance with the present invention, a computer may be programmed to utilize optimal control theory in conjunction with SFC (or any form of chromatography) to provide a formulation and solution to the optimal resolution problem whose objective is to find the dynamic operating characteristics of the process variable which provide a particular resolution in the fastest analysis time, without the need for expensive trial and error procedures.

On one embodiment of the invention, which utilizes supercritical fluid chromatography, the critical system parameters, such as, for example, the length of column, type of analytes, type of substrate, particular transport medium, and the relationship of capacity factor k to either temperature (as illustrated in FIG. 3) or pressure and density of the transport medium, are stored in the computer memory. To determine the fastest analysis time that may be employed to obtain a particular level of resolution, the system is initialized by inputting or storing in the computer the variable parameters of the chromatographic system, such as a desired analysis time, and the desired resolution, which may be, for example, in the form of the distance between peak means. The computer has a program or programs stored therein which use an objective function together with certain algorithmic relationships, described further hereinbelow, to predict the process variable needed to provide a particular resolution within a suitable analysis time or alternatively, the fastest analysis time.

If the resultant chromatogram from the computer generated analysis illustrates more than adequate resolution, the analysis can be repeated with a shorter time period. Conversely, if the program is not capable of producing the desired resolution in the analysis time that was inputted into the system, the analyses can be repeated using a longer analysis time. Alternatively, the program may be designed to rerun itself again and again until optimized performance is attained. In this manner, the system can predict in seconds results that heretofore required hours or even days of experimenting.

Alternatively, the program ma be set up to rerun itself until the difference between the desired resolution and that predicted using the program was less than a certain threshold value, which may be either permanently stored in the computer, or entered prior to a run.

The invention utilizes a thermodynamic model in conjunction with a dynamic model for the species' evolution through the column. The thermodynamic model is for the capacity factor for each species. In one embodiment of the present invention, for SFC, the capacity factor model is given by the following mathematical form:

$$k_i(\rho) = a_j \frac{\rho}{\rho_o} - b_j \tag{1}$$

for each species where $\rho_0$ is a reference density for the mobile phase, $\rho$ is any other density of this phase, $k_i(\rho)$ is the capacity factor for the species (i) at density $\rho$. The terms $a_j$ and $-b_j$ are model parameters. A thermodynamic model and a SCF chromatographic column model has been described in an article by Kelley and Chimowitz, entitled "A New Representation for Retention Time in Supercritical Fluid Chromatrogaphy", J. Supercritical Fluids, Vol. 2, pp. 106–110 (1989). The a and b model parameters are constants, or model parameters, which are evaluated from thermodynamic data, as explained in this 1989 article by Kelley & Chimowitz. The values of $k_i(\rho)$ at two densities is sufficient to establish values for $a_j$ and $-b_j$ which define the thermodynamic model for species i. This is required for each species.

Similar expressions for capacity factor are either available or can be easily calculated for other forms of chromatography.

For example, for gas chromatography, a suitable capacity factor model is:

$$k_{(i)}(t) = A + \frac{B}{T}, \tag{2}$$

where A and B are model parameters and T is temperature. A suitable equation for the capacity factor in liquid chromatography is:

$$k = A + BC, \quad (3)$$

where A and B are model parameters, and C is composition.

In accordance with the SFC capacity factor model, the dynamic evolution of each species through the packed bed in the SFC column may be represented by the following equation:

$$\frac{\partial (1+k)c}{\partial t} = D \frac{\partial^2 c}{\partial x^2} - \frac{\partial}{\partial x}\left(\left(\frac{\dot{m}_o + A(L-x)\frac{d\rho}{dt}}{A\rho}\right)c\right) \quad (4)$$

$$i = 1, \ldots, n$$

where
c = species concentration
t = time
D = diffusion coefficient, species i
x = axial length down the bed
$\dot{m}_0$ = input mass flow rate to column
A = cross-sectional area of the bed
L = length of column
$\rho$ = mobile phase fluid density
n = number of species being separated
k = capacity factor (thermodynamic partition coefficient)

However, this equation does not contain the most important variable, time of residence in the column, and consequently is inadequate for resolution vs. time optimization. In accordance with the invention a velocity relationship has been discovered which describes the species distance—dependence throughout the column. This relationship also contains the dynamic density term $$\left(\frac{d\rho}{dt}\right),$$

which represents the rate of change of density element explicitly. It is expressed in equation (5)

$$u_j = \frac{1}{1+k_j}\left(\frac{\dot{m}_o + A(L-x_j)\frac{d\rho}{dt}}{A\rho}\right) \quad (5)$$

where $u_j$ is the velocity at which component j is moving through the column and $k_j$ is the capacity factor of component j. The velocity is in fact the time derivative of the distance or:

$$u_j = \frac{dx_j}{dt} = \frac{1}{1+k_j}\left(\frac{\dot{m}_o + A(L-x_j)\frac{d\rho}{dt}}{A\rho}\right) \quad (6)$$

$$j = 1, \ldots, n$$

Consequently, equation (6) above shows the relationship between time dependence of the mobile phase density the species adsorption capacity factor $k_j$ (j is the respective species), the mass flow rate $\dot{m}_0$ of the mobile phase into the column, the column cross-section area A, the column length L, the distance traveled in the column $x_j$ by species j, the fluid density $\rho$, and the time of the analysis t. Thus equation (6) contains the essential dynamic information needed to model residence times behavior of each of the analyte species.

Thus, the present invention models the column behavior and provides the relationships for optimizing the separation performance. Using the capacity factor model for SFC described hereinabove (equation 1), the relationship between resolution vs. time can e optimized using the following objective function:

$$(x_N(t_f) - L)^2 + \int_0^{t_1} \sum_{j=1}^{N-1} (x_j(t) - x_{j+1}(t) - \Delta_j)^2 \quad (7)$$

Where $x_j$ is the distance travelled in the column by component j. The components are numbered from fast (j=1) to slow (j=N). L stands for the length of the column and $\Delta_j$ is the resolution term, which in this case represents the distance by which the means of two neighboring peaks have to be separated. The parameter $t_f$ is the specified time within which the separation has to be completed. The first term of equation (7), $(x_N(t_f) - L)^2$ is a static term that requires the slowest component to emerge from the column at the specified time $t_f$. The last term (the term under the integral sing) is the dynamic part of the function, and relates to the required resolution between components. This term requires that peak pair (j) and (j+1) be separated by $\Delta_j$ after $t_f$. By specifying successively smaller values for $t_f$ under computer control we can optimize system performance by looking for satisfactory resolution ($\Delta_j$) in the fastest possible time.

The optimization process involves minimizing the above objective function subject to the dynamic constraints dictated by equation (6) above. By doing so, the optimal density trajectory relationship, which may be expressed as density $\rho$ vs. time, can be obtained. It should be noted that the exact objective function utilized is not critical to the invention. Thus, for example, alterations could be made to the above objective function (7) without departing from the scope of the invention.

If desired, weighting factors may be employed to express the relative importance of the separation between the component couples and analysis time. For example, in the following function, $W_0$ is a weighting factor employed to express the relative importance of the time term, and $W_j$ is a weighting factor employed to express the relative importance of resolution:

$$W_o(x_N(t_f) - L)^2 + \int_0^{t_1} \sum_{j=1}^{N-1} W_j(x_j(t) - x_{j+1}(t) - \Delta_j)^2 \quad (8)$$

Thus, for example, if $W_0$ is a given large number relative to $W_j$, the objective function will emphasize time of analysis over resolution, and given a small $W_0$ relative to $W_j$ the objective function will emphasize resolution.

The Algorithmic Description of Optimal Density Programming

The optimal control algorithm optimizes the dynamic behavior of all the species' residence time distributions given by dynamic equations similar to equation (5), according the pre-specified objective function, in this case given by equation (7). Further information concerning the algorithm may be found in "Separation in Packed Beds Using Supercritical Fluids", Catholic University Leuven (Belgium) (January 1992). For this numerical analysis a model for the various species' k (capacity factor) is required. As mentioned above, for supercritical fluid chromatography, the following expression for capacity factor may be used:

$$k_j = a_j \frac{\rho}{\rho_0} {}^{-b_j}$$

Where $a_j$ and $b_j$ are constants evaluated from thermodynamic data (See J. Supercritical Fluids, Vol. 2, pp 106–110 (1989), $\rho$ is the mobile phase density, $\rho_0$ a reference phase density.

Computational Algorithms

The present numerical solution to the optimal control problem is given as the minimization of the objective function (7) subject to the constraint given by equation (5) above for each species.

The theory requires an objective function and equation modeling the system dynamic behavior to be provided. These dynamic equations have control variables imbedded in their formulation. These variables are free to be manipulated dynamically with time. The purpose of the theory is to provide a description of the dynamic control variable trajectories that best meets the process objectives as specified in the objection function.

Mathematically this requires the formulation of the system Hamiltonian from the specified objective function and dynamic modeling equation. The optimal trajectories for the control variables, here designated as $u_i[t]$ are the ones that satisfy the Hamiltonian condition given as $dH/d_{u(i)} = 0$ for $i=1,N$ where there are N control variables and H is the system Hamiltonian.

Quantitative Problem Formulation

In a preferred embodiment of the invention, the following equations are used to calculate the optimal density profiles.

The evolution of the different peaks is modeled by the differential equation:

$$\frac{dx_j}{dt} = \phi_j(t) = \frac{1}{1 + k_j} \left( \frac{\dot{m}_o + A(L - x_j)\frac{d\rho}{dt}}{A\rho} \right) \quad (9)$$

$$i = 1, \ldots, n$$

The system Hamiltonian is defined to e:

$$H = F(x,t) + \sum_{j=1}^{n} \lambda_j \phi_j(x_j,t) \quad (10)$$

or using objective function given in (7):

$$H = \sum_{j=1}^{N-1} (x_j - x_{j+1} - \Delta_j)^2 + \sum_{j=1}^{N} \lambda_j(t)\phi_j(t) \quad (11)$$

From this equation it is obvious that the Hamiltonian is an explicit function of the $x_j$, t and $\lambda_j$ (the adjoint variables).

The controlling parameter in the case of the density gradient programming in SFC is the density trajectory $\rho(t)$. Since $\rho$ only appears in the modeling equation and not in the performance index, the gradient of the Hamiltonian is written as;

$$\frac{\partial H}{\partial \rho} = \sum_{j=1}^{N} \lambda_j(t) \frac{\partial \phi_j}{\partial \rho} \quad (12)$$

The derivative of the modeling equation is given by:

$$\frac{\partial \phi_j}{\partial \rho} = \frac{\partial}{\partial \rho} \left( \frac{1}{1 + a_j \left(\frac{\rho}{\rho_0}\right)^{-b_j}} \frac{\dot{m}_o + A(L - x_j)\frac{d\rho}{dt}}{A\rho} \right) \quad (13)$$

where we have used the previously mentioned thermodynamic model for $k_j$. Differentiating the whole expression through leaves us with the final expression for the gradient of the Hamiltonian:

$$\frac{\partial \phi_j}{\partial \rho} = \left( \frac{\dot{m}_o + A(L - x_j)\frac{d\rho}{dt}}{A\rho} \right) \frac{1}{1 + a_j \left(\frac{\rho}{\rho_0}\right)^{-b_j}} \left(\frac{1}{\rho}\right) + \left[ -1 + \frac{1}{1 + a_j \left(\frac{\rho}{\rho_0}\right)^{-b_j}} \left( a_j b_j \left(\frac{\rho}{\rho_0}\right)^{-b_j} \right) \right] \quad (14)$$

The adjoints have to satisfy:

$$\frac{d\lambda_j}{dt} = -\left(\frac{\partial H}{\partial x_j}\right) \quad (15)$$

with the boundary condition:

$$\lambda_j(t_f) = \left(\frac{\partial G}{\partial x_j}\right) \quad (16)$$

Translating these equations into our problem formulation, gives the complete expression for the adjoints. The differential model for the calculation of the Lagrangian multiplier anoints is thus given by:

$$\frac{d\lambda_1}{dt} = -\left( (x_1 - x_2 - \Delta_1) - \lambda_1 \frac{1}{1 + k_1} \frac{1}{\rho} \frac{d\rho}{dt} \right) \quad (17)$$

$$\frac{d\lambda_j}{dt} = (x_j - x_{j+1} - \Delta_j) + (x_{j-1} - x_j - \Delta_{j-1}) + \lambda_j \frac{1}{1 + k_j} \frac{1}{\rho} \frac{d\rho}{dt} \quad (18)$$

$$(1 \neq j \neq N)$$

$$\frac{d\lambda_N}{dt} = \left( (x_{N-1} - x_N - \Delta_{N-1}) - \lambda_N \frac{1}{1 + k_N} \frac{1}{\rho} \frac{d\rho}{dt} \right) \quad (19)$$

The initial conditions for the adjoint variables $\lambda_j$, except for the one connected with the slowest component are given by:

$$\lambda_j(t_f) = \frac{\partial G}{\partial x_j} = 0 \qquad (20)$$

$$j = 1, \ldots N - 1$$

The other initial condition for the slowest component is given by:

$$\lambda_N(t_f) = \frac{\partial G}{\partial x_N} = 2W_o(x_N - L) \qquad (21)$$

All these equations are implemented in the programs or described in the charts of FIGS. 9-11 which cover various forms of chromatography.

The particular form of objective function, equation (7), utilized will determine the exact form of the Langranian multiplier adjoint equation. The only required and necessary stipulations for the objective function are that first it must contain a term representative of some form of chromatographic resolution, and second it must contain a term representing time of analysis. The particular function forms utilized to represent these two terms will dictate and be embodied in the resultant Lagrangian multiplier adjoint equations.

The method of deriving Lagrangian multiplier adjoint equation from a particular objective function (7) is well known in the art, and for example is explained in "Advanced Process Control", W. H. Ray, McGraw-Hill Books, pp. 88 et. seq. (1981).

Information Flow For Optimizing SFC

With reference to FIG. 6, a flow diagram is provided for an SFC optimizing program. As shown in FIG. 6, in a preferred embodiment of the invention the main steps in the computation are as follows:

1. Establish and input into a computer the following parameters for the system: (1) an expression for the capacity factor model $k_i(\rho)$ for each species i for the particular column and transport medium to be used, as discussed hereinabove.

For example, for SFC, the capacity factor expression would be $$k_j = a_j \frac{\rho}{\rho_o}^{-b_j};$$

(2) the flow rate of the transport medium; (3) the column length L; (4) cross-sectional area of the column; (5) the time of analysis $t_f$ desired by the technician; (6) a term representing resolution. This can be in any form operable to measure resolution. For purposes of illustration, this term is $\Delta_j$, which defines the distance between species emerging from the column; (7) a particular desired resolution index range Rmin to Rmax for the entire chromatogram which defines the range of the resolution of all of the species being analyzed. The range Rmin to Rmax may be expressed in any form for measuring chromatographic resolution, such as, for example, the distance between the means of peaks, the time between the means of peaks, the spread of peaks, etc. In addition, the particular value chosen for the resolution index R specifies the degree of resolution desired by the technician.

2. Assume an initial density trajectory $(\rho_{(t)})$ over time for the particular transport medium and time interval $t_f$ established in step 1. Of course, accurately guessing the density trajectory will be facilitated as the experience of the technician grows. However, extreme accuracy in guessing the initial trajectory is not absolutely necessary to optimize the relationship between resolution and time of analysis in accordance with the invention. In such cases where, for example, the experience of the technician is limited, a density trajectory equal to the transport medium critical density $\rho_c$ and constant over time, is an adequate initial prediction.

3. Using the density trajectory guessed in step 2, and the column parameters established in step 1, numerically integrate the following n dynamic equations which illustrate (to yield relationships for) (showing) the dynamic positions of each species n with time along the column axial direction. The equation for each species (n equations for n species) is given by:

$$\frac{dx_j}{dt} = \frac{1}{1 + k_j} \left( \frac{\dot{m}_o + (L - x_j)A \frac{d\rho}{dt}}{A\rho} \right) \qquad (22)$$

4. Using the given density trajectory and the solutions of the equation integrated in step 3 which provides $x_i(t)$ vs. time (from $t_0$, which $=0$, to $t_f$), numerically backward in time over the time interval $t_f$ to $t_0$:

$$\frac{d\lambda_1}{dt} = -\left( 2(x_1 - x_2 - \Delta_1) - \lambda_1 \frac{1}{1 + k_1} \frac{1}{\rho} \frac{d\rho}{dt} \right) \qquad (23)$$

$$\frac{d\lambda_j}{dt} = -2(x_j - x_{j+1} - \Delta_j) + 2(x_{j-1} - x_j - \Delta_{j-1}) + \qquad (24)$$

$$\lambda_j \frac{1}{1 + k_j} \frac{1}{\rho} \frac{d\rho}{dt}$$

$$(1 \neq j \neq N)$$

$$\frac{d\lambda_N}{dt} = \qquad (25)$$

$$-\left( -2(x_{N-1} - x_N - \Delta_{N-1}) - \lambda_N \frac{1}{1 + k_N} \frac{1}{\rho} \frac{d\rho}{dt} \right)$$

This yields the relationships $\lambda_i[t]$ from $t_f$ to $t_0$ for each multiplier variable $\lambda_i$ (i = 1 . . . N).

5. Calculate a trajectory representing the correction in density at each point in time (i.e., a correction for density profile) throughout the interval $t_0$ to $t_f$ using the following equation:

$$\frac{\delta H}{\delta \rho} = \sum_{j=1}^{N} \lambda_j(t) \frac{d\phi_j}{d\rho} \qquad (26)$$

where $$\frac{d\phi_j}{d\rho} = \frac{\delta}{\delta \rho} \left( \frac{1}{1 + k_j} \frac{\dot{m}_o + (L - x_j)A \frac{d\rho}{dt}}{A\rho} \right) \qquad (27)$$

6. Determine the optimal scaling factor or correction factor $\epsilon_{opt}$ using a one dimensional line search method. This procedure designates the optimal change in density at each point in time. Alternatively, a reasonable guess could be made for $\epsilon_{opt}$.

Preferably, however, a line search (also known as a one-dimensional search) technique is used to determine $\epsilon_{opt}$. Line searching is a well-known single variable optimization technique, and is explained, for example, in Introduction to Linear and Non-linear Programming, by Luenberger, Addison-Wesley Publishing, pp. 33 et. seq. (1973).

7. Calculate a "new" density trajectory $\rho(t)$ at each point in time over the time interval $[t_0, t_f]$ using the following equation:

$$\rho(t)^{new} = \rho(t) - \epsilon_{opt} \frac{\delta H}{\delta \rho} \qquad (28)$$

8. Calculate the difference between the new density trajectory and the old density trajectory. If this difference is greater than a pre-selected threshold value, the above process is repeated, beginning with step 3, with the new density trajectory. As this process is repeated, the new density trajectory which is calculated each time moves closer and closer to the optimal density trajectory. Once the difference between $\rho(t)_{new}$ and $\rho_{old}$ is less than the threshold value, the reiteration process stops, and the $\rho(t)_{new}$ that satisfied the threshold is utilized for step 9.

9. $\rho(t)_{new}$ which satisfied the threshold relationship described in step 8 is used to simulate the behavior of the column performance using a computational procedure described in "An Algorithm for the Simulation of Density-Programmed Supercritical Fluid Chromatography", Van Puyvelde and Chimowitz, J. Supercritical Fluids, Vol. 3, pp. 127–135 (1990).

10. The technician may now visualize the simulated chromatogram obtained by using the new density trajectory and adjust the time interval allowed for analysis depending on whether more or less resolution is needed. Alternatively, the program can be tailored to automatically calculate a resolution index R* for the predicted chromatogram and compare R* to $R_{min}$ and $R_{max}$. R* may represent, for example, the same type of resolution, such as distance between mean peaks, etc., that was initially specified as $R_{min}$ and $R_{max}$. This may or may not be the same resolution specified by the objective function. In any event, R* is compared to $R_{max}$, and if R* is greater than $R_{max}$, the resolution is greater than necessary, and consequently the time interval inputted may be decreased. If R* is less than $R_{min}$, then resolution is less than required, and the time interval $[t_0 - t_f]$ must be lengthened. The increase or decrease in time interval may be performed via the technician directly or, alternatively, the program may be tailored to automatically adjust the time interval and rerum the above calculations. Once R* falls between $R_{min}$ and $R_{max}$, the density profile is considered optimized (i.e., the required resolution is being obtained within the fastest time).

The present invention is useful for obtaining the operating parameters necessary to obtain a certain degree of resolution in a reasonable amount of time for a given chromatographic system. The present invention is able to match the experimental data of Wilsch and Schneider, for example, who were able to provide a dynamic density profile established only after much experimental trial-and-error.

The present invention is operable with any form of chromatographic system to be analyzed. The thermodynamic model for each species' capacity factor can be found from experimental data as discussed hereinabove and in "Retention and Resolution in Density Pro-grammed Supercritical Fluid Chromatography", Wilsch et. al., J. Chromatography, Vol. 357, No. 239 (1986). Given a conventional SFC device the output from the optimal control algorithm is fed to a pump or regulator valve (such as 6 in FIG. 1) that adjusts mobile phase flow rates to track the optimal density profile. Flow diagrams similar to FIG. 6 are provided for gas chromatography (in FIG. 7), and liquid chromatography (in FIG. 8).

The sequence of operations is basically the same regardless of the type of chromatography being utilized, with the exception of the expression of capacity factor, and the resultant Lagrangian multipliers and derivatives of the Hamiltonian equations.

EXAMPLE 1

Figure 4:
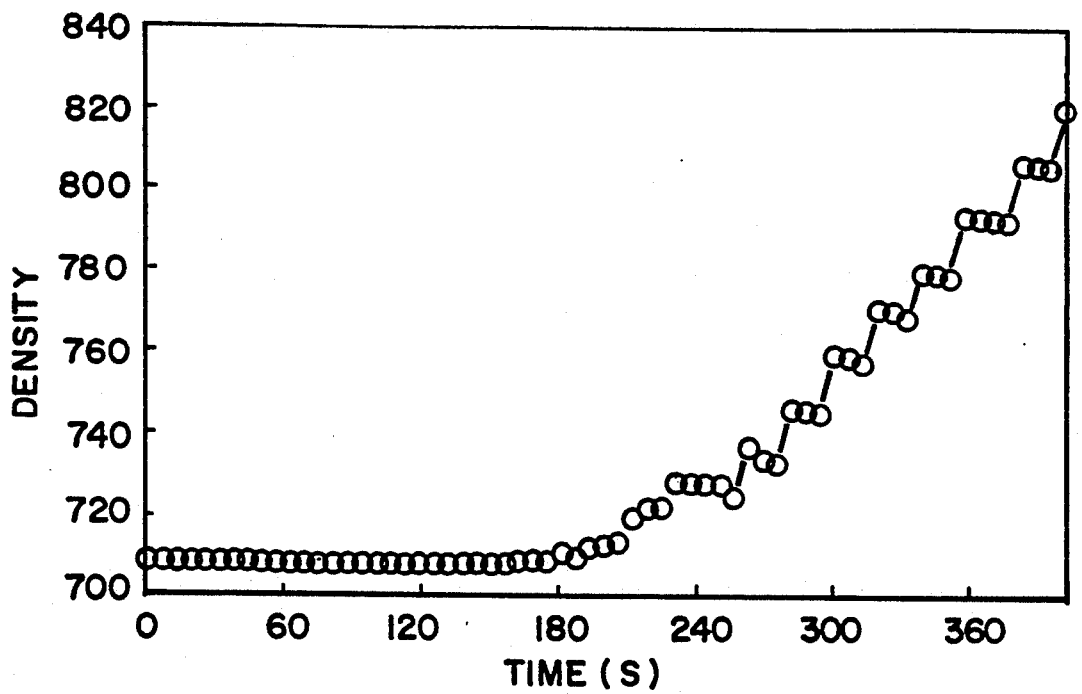
FIG. 4 is a plot of a supercritical fluid density profile calculated in a system embodying the present invention.
Figure 5:
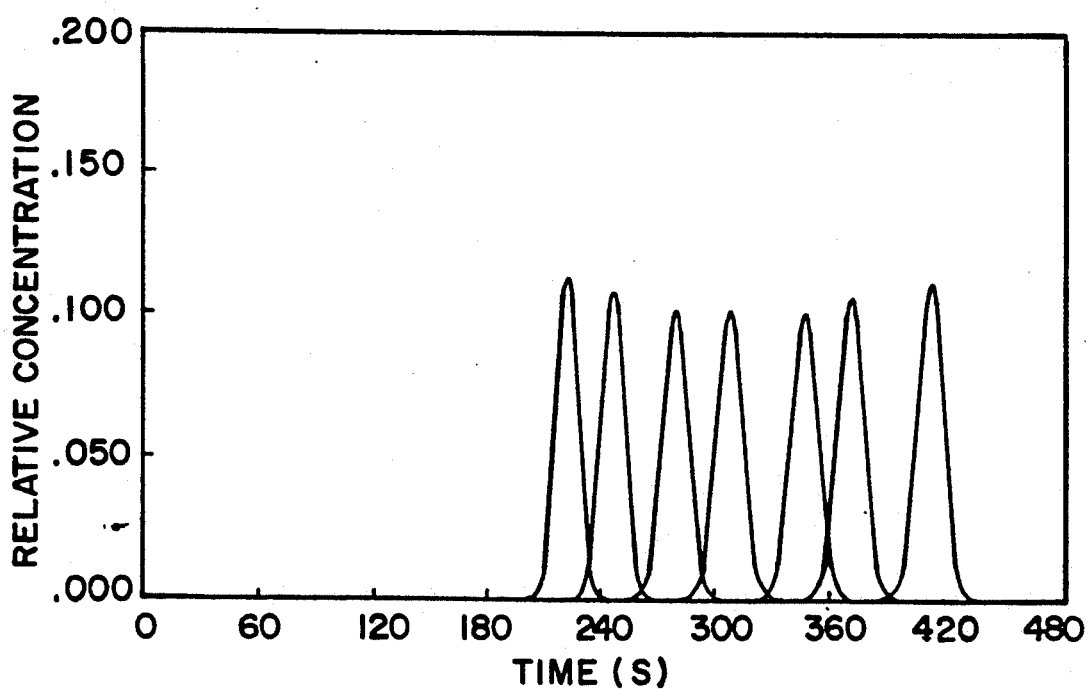
FIG. 5 is an illustration of a chromatogram for the same chromatographic system used to produce FIG. 2, but simulated in accordance with the present invention using the density profile of FIG. 4.

This example compares results obtained using the method of the present invention to actual SFC experimental data give by Wilsch and Schneider (1986). The chemistry of the system and column details are shown in Tables 1 and 2. In their paper Wilsch and Schneider describe a very laborious trial-an-error procedure for attempting to optimize system performance by doing repetitive experimental analyses. The procedure is extremely time-consuming. The chromatogram obtained using this procedure is illustrated in FIG. 2. The invention in operation yielded the dynamic supercritical fluid density profile shown in FIG. 4. This density profile shows precisely how the density for the mobile phase is to be controlled with time to yield optimal resolution. Using this density profile, a chromatograph was simulated in accordance with the present invention and is illustrated in FIG. 5. These results agree very closely with the experimental data obtained by trial and error by Wilsch and Schneider, illustrated in FIG. 2, yet were generated by the optimal control algorithm in a matter of a few minutes.

The invention has been described in detail with articular reference to preferred embodiments thereof, but it will be understood that variations and modifications can be effected within the spirit and scope of the invention.

For example, most of the SFC discussion and flow charts, etc., deal with a capacity factor model based on density. However, the capacity factor model could be based on temperature and/or pressure, as discussed in "Near Critical Phenomena and Resolutions in Supercritical Fluid Chromatography", Kelley and Chimowitz, AIchE Journal, Vol. 36, No. 8, pp 1163–1175 (August 1990). If the capacity factor model were based on temperature and/or pressure, the resultant objective functions and Hamiltonian equation would likewise have to change, but those skilled in the art could do so without departing from the spirit and scope of the invention.

Also, most of the discussion herein has dealt with optimizing the time/resolution relationship of chromatograms using all of the species contained in the analyte sample. However, in some cases, the number of separate species in the analyte sample could be large (for example, 100 species in some materials is possible), in which case, if desired, the operation of the invention could be utilized using only a fraction of the total number of species in the analyte sample.

We claim:

1. The system for chromatographic analysis comprising:

(a) a column having a stationary substrate phase therein;

(b) said column also having a mobile transport phase having a capacity factor representing the ability of the mobile phase to transport a species under analysis through said column;

(c) detector means for dynamically measuring the time of migration of said species through said column;

(d) reporting means responsive to said dynamic migration time measurements for providing a chromatogram having data corresponding to said species; and (e) computer means for processing said data for optimizing the relationship between resolution of the chromatogram provided by said reporting means and time; said computer means comprising (i) means responsive to said chromatogram for calculating the capacity factor for each of the species under analysis, and (ii) means responsive to the capacity factor and physical parameters of the system including the column length and type of substrate and properties of the mobile transport phase selected from the group consisting of density, temperature and composition of the mobile phase.

2. The invention as set forth in claim 1 wherein said capacity factor changes over time and has a rate of change, and said computer means includes means responsive to the rate of change of the capacity factor.

3. The invention as set forth in claim 1, wherein said computer means includes means for calculating the minimum amount of time needed to obtain a desired resolution.

4. The invention as set forth in claim 1 wherein said computer means further comprises means for calculating the properties, selected from the group consisting of density and temperature needed to produce a desired resolution in a particular time period.

5. The invention as set forth in claim 1, wherein said computer means includes means responsive to an objective function which represents the chromatographic process, the objective function having (a) a time of analysis term and (b) a resolution term.

6. The invention as set forth in claim 5, wherein said computer means has means responsive to said objective function to calculate Lagrangian multiplier adjoint equations.

7. The invention as set forth in claim 5, wherein said computer means has means responsive to said objective function to calculate a plurality of outputs representing the derivative of a Hamiltonian equation with respect to a set of control variables.

8. The invention as set forth in claim 5, wherein said computer means has means responsive to the following objective function for optimizing the relationship between resolution of the reporting means and time;

$$(x_N(t_f) - L)^2 + \int_0^{t_1} \sum_{j=1}^{N-1} (x_j(t) - x_{j+1}(t) - \Delta_j)^2$$

where
$x_j$ = distance traveled in the column by the component j
$L$ = length of the column
$\Delta_j$ = distance between peaks
$t_f$ = time of analysis
$t_0$ = initial time (0)

9. The invention as set forth in claim 1, wherein said mobile phase is a supercritical fluid.

10. The invention as set forth in claim 9, wherein said computer means has means for adjusting the capacity factor of the mobile phase by adjusting one or more of the parameters pressure, density and temperature within the chromatographic system.

11. The invention as set forth in claim 9, wherein said computer means has means for providing outputs corresponding to the pressure and temperature needed, for a given combination of substrate, species under analysis, and mobile phase supercritical fluid, to obtain a particular resolution in a particular time period.

12. The invention as set forth in claim 11, wherein said time period is a minimum time period.

13. A method of optimizing the relationship between resolution and time in a SCF chromatographic system having a column along which j analyte components are transported by a SFC mobile phase to provide a chromatogram having peaks separate by distances $x_j(t)$ corresponding to the time for each of the j components to be transported to a downstream end of said column certain resolution in a optimally short period of time, comprising the steps of:

inputting an initial density profile $\rho(t)$ over time for the supercritical fluid mobile phase;
measuring $x_j(t)$ from said peaks;
integrating the following modeling equation for the number of the analyte components j using the initial density profile;

$$\frac{dx_j}{dt} = \frac{1}{1+k_j} \left( \frac{m_0 + (L - x_j)A \frac{d\rho}{dt}}{A\rho} \right)$$

where
t = time
x = axial length down the column
$m_0$ = input mass flow rate to column
A = cross-sectional area of the bed
L = length of column
$\rho$ = mobile phase fluid density of the SCF
j = number of species being separated
$k_j$ = capacity factor (thermodynamic partition coefficient) for the j component integrating the following Lagrangian multipliers backward in time over $[t_0, t_f]$ using the density profile $(\rho(t))$ and the peaks $x_j(t)$;

$$\frac{d\lambda_1}{dt} = -\left( 2(x_1 - x_2 - \Delta_1) - \lambda_1 \frac{1}{1+k_1} \frac{1}{\rho} \frac{d\rho}{dt} \right)$$

$$\frac{d\lambda_j}{dt} = -2(x_j - x_{j+1} - \Delta_j) + 2(x_{j-1} - x_j - \Delta_{j-1}) +$$

$$\lambda_j \frac{1}{1+k_j} \frac{1}{\rho} \frac{d\rho}{dt}$$

$(1 \neq j \neq N)$ $$\frac{d\lambda_N}{dt} =$$

$$-\left( -2(x_{N-1} - x_N - \Delta_{N-1}) - \lambda_N \frac{1}{1+k_N} \frac{1}{\rho} \frac{d\rho}{dt} \right)$$

calculating a correction in density profile using the following equation;

$$\frac{\delta H}{\delta \rho} = \sum_{j=1}^{N} \lambda_j(t) \frac{d\phi_j}{d\rho}$$ 5 where $$\frac{d\phi_j}{d\rho} = \frac{\delta}{\delta \rho} \left( \frac{1}{1 + k_j} \frac{m_o + (L - x_j)A \frac{d\rho}{dt}}{A\rho} \right)$$ 10 and changing the density of said SCF in said column according to said correction.

14. The method as set forth in claim 13, further comprising the steps of:
using a one dimensional search technique to determine an optimal scaling factor $\epsilon_{opt}$; and
calculating an improved density profile $\rho(t)^{new}$ using the following equation;

$$\rho(t)^{new} = \rho(t) - \epsilon_{opt} \frac{\delta H}{\delta \rho}.$$

15. The method as set forth in claim 14, further comprising:
determining the difference between $\rho(t)$ and $\rho(t)^{new}$; and
if said difference is greater than a chosen threshold value, recalculating optimum density by setting the initial density profile=$\rho(t)^{new}$ and repeating the steps set forth in claims 13 and 14.

16. A method for calculating an optimum temperature profile for a gaseous transport fluid which transports along a column of analyte components to be analyzed to obtain a chromatogram with peaks corresponding to the j components particular resolution in the shortest time in a gas chromatographic system having said column, comprising:
initializing the system by inputting an initial temperature profile T(t) over the time interval [$t_0,t_f$] for the gas;
measuring the distance $x_j(t)$ which corresponds to the time which it takes for each of the j components to travel along the column by the separation distance of the peaks;
integrating the following modeling equation for each component j using the initial temperature profile;

$$\frac{dx_j}{dt} = \frac{1}{1 + k_j} \left( \frac{m_o}{A\rho} \right)$$

where
t=time
x=axial length down the column
$m_0$=input mass flow rate to column
A=cross-sectional area of the bed
L=length of column
$\rho$=mobile phase fluid density of the SCF
j=number of species being separated
$k_j$=capacity factor (thermodynamic partition coefficient) for the j component
integrating the following Lagrangian multipliers backward in time over [$t_0,t_f$] using the temperature profile (T(t)) and the peaks $x_j(t)$;

$$\frac{d\lambda_1}{dt} = -(x_1 - x_2 - \Delta_1)$$

$$\frac{d\lambda_j}{dt} = -(x_j - x_j + 1 - \Delta_j) + (x_{j+1} - x_j - \Delta_{j-1})$$

$(1 \neq j \neq N)$ $$\frac{d\lambda_N}{dt} = -(-2(x_{N-1} - x_N - \Delta_{N-1}))$$

calculating a correction in temperature profile using the following equation;

$$\frac{\delta H}{\delta T} = \sum_{j=1}^{N} \lambda_j(t) \frac{d\phi_j}{dT}$$

where $$\frac{d\phi_j}{dT} = \frac{\delta}{\delta T} \left( \frac{1}{1 + k_j} \frac{m_o}{A\rho} \right)$$

and changing the temperature of the gas in the column in accordance with the correction.

17. The method as set forth in claim 16, further comprising the steps of:
using a one dimensional search technique to determine the optimal scaling factor $\epsilon_{opt}$; and
calculating a new temperature profile using the following equation:

$$T(t)^{new} = T(t)^{old} - \epsilon_{opt} \frac{\delta H}{\delta T}.$$

18. The method as set forth in claim 17, further comprising:
determining the difference between T(t) and T(t)$^{new}$; and
if said difference is greater than a chosen threshold value, regulating optimum temperature profile by setting the initial density profile=T(t)$^{new}$ and repeating the steps set forth in claims 16 and 71.

19. A method for calculating an optimum composition profile of a liquid transport fluid to obtain a particular resolution in the shortest time in a liquid chromatographic system which provides a chromatogram having a plurality of spaced peaks corresponding to a plurality j of analyte components which are transported along a column, the peaks being separated by distances xj(t) which correspond to the time it takes for each of the j components to be transported along the column, comprising:
initializing the system with an initial composition profile c(t) over time for the liquid transport fluid;
measuring xj(t) from the peaks;
integrating the following modeling equation for each component j using the initial composition profile;

$$\frac{dx_j}{dt} = \frac{1}{1 + k_j} \left( \frac{m_o}{A\rho} \right)$$

where
t=time
x=axial length down the column
$m_0$=input mass flow rate to column
A=cross-sectional area of the bed L = length of column
ρ = mobile phase fluid density of the SCF
j = number of species being separated
kj = capacity factor (thermodynamic partition coefficient) for the j component integrating the following Langrangian multipliers backward in time over $[t_0, t_f]$ using the composition profile (c(t)) and the peaks $x_j(t)$;

$$\frac{d\lambda_1}{dt} = -(2(x_1 - x_2 - \Delta_1))$$

$$\frac{d\lambda_j}{dt} = -2(x_j - x_{j+1} - \Delta_j) + 2(x_{j-1} - x_j - \Delta_{j-1})$$

$$(1 \neq j \neq N)$$

$$\frac{d\lambda N}{dt} = -(-2 x_{N-1} - x_N - \Delta_{N-1}))$$

calculating a correction composition profile using the following equation;

$$\frac{\delta H}{\delta c} = \sum_{j=1}^{N} \lambda_j(t) \frac{d\phi_j}{dc}$$

where $$\frac{d\phi_j}{dc} = \frac{\delta}{\delta c}\left(\frac{1}{1+k_j} \frac{m_o}{A\rho}\right)$$

and changing the composition of said liquid in accordance with said correction.

20. The method as set forth in claim 19, further comprising the steps of:
using a one dimensional search technique to determine the optimal scaling factor $\epsilon_{opt}$; and
calculating a new composition profile $c(t)^{new}$ using the following equation;

$$c(t)^{new} = c(t)^{old} - \epsilon_{opt} \frac{\delta H}{\delta c}.$$

21. The method as set forth in claim 20, further comprising:
determining the difference between c(t) and $c(t)^{new}$; and
if said difference is greater than a chosen threshold value, recalculating optimum composition profile by setting the initial composition profile = $c(t)^{new}$ and repeating the steps set forth in claims 19 and 20.

* * * * *